(12) United States Patent
Campbell et al.

(10) Patent No.: US 8,404,288 B2
(45) Date of Patent: Mar. 26, 2013

(54) MICROBIALLY-STABLE VITAMIN E SOLUTIONS

(75) Inventors: Marta Campbell, Florence, KY (US); Robert Joseph Sarama, Loveland, OH (US)

(73) Assignee: Sunny Delight Beverage Company, Cincinnati, OH (US)

( * ) Notice: Subject to any disclaimer, the term of this patent is extended or adjusted under 35 U.S.C. 154(b) by 275 days.

(21) Appl. No.: 12/843,110

(22) Filed: Jul. 26, 2010

(65) Prior Publication Data

US 2011/0027424 A1 Feb. 3, 2011

Related U.S. Application Data

(60) Provisional application No. 61/230,148, filed on Jul. 31, 2009.

(51) Int. Cl.
*A23L 1/302* (2006.01)
(52) U.S. Cl. ............ 426/72; 426/74; 426/310; 426/311; 426/321; 426/590
(58) Field of Classification Search .................... 426/74, 426/72, 590, 310, 311, 321
See application file for complete search history.

(56) References Cited

U.S. PATENT DOCUMENTS

| 5,417,994 | A | 5/1995 | Chang et al. | |
|---|---|---|---|---|
| 2005/0084602 | A1* | 4/2005 | Chen et al. | 426/654 |
| 2005/0095320 | A1 | 5/2005 | Botteri et al. | |
| 2009/0017167 | A1 | 1/2009 | Krumhar et al. | |

FOREIGN PATENT DOCUMENTS

| CN | 101 199 273 | 6/2008 |
|---|---|---|
| CN | 101 690 547 | 4/2010 |
| GB | 985 613 | 3/1965 |
| JP | 2000247879 A * | 9/2000 |
| WO | WO 99/07238 | 2/1999 |
| WO | WO 02/87326 | 11/2002 |
| WO | WO 02/087326 WO | 11/2002 |
| WO | WO 03/043446 | 5/2003 |
| WO | WO 2004/095952 | 11/2004 |

OTHER PUBLICATIONS

Abstract for CN 101 199 273.
Abstract for CN 101 690 547.
Certificate of Analysis—TPGS—Vitamin E Polyethylene Glycol Succinate, Food Grade, PN: TG0101FG, TG0115FG and TG0150FG, Lot TBOC0109002 (Jan. 2009) p. 1.
"Material Safety Data Sheet," Antares Health Products, Inc. (Nov. 15, 2006) pp. 1-4.
Product Data—TPGS—Vitamin E. Polyethylene Glycol Succinate, Food Grade, PN: TB0101FG and TG0115FG, CAS Reg. No. 9002-96-4 (Nov. 15, 2006) pp, 1-2.
Abstract for Chinese Application CN 101 199 273, published Jun. 18, 2008, by applicant Guangzhou Yousheng Biotechnolo, downloaded Jun. 7, 2011 from http://worldwide.espacenet.com.
Abstract for Chinese Application CN 101 690 547, published Apr. 7, 2010, by applicant Anhwei Tiger Biotech Co. Ltd., downloaded Jun. 7, 2011 from http://worldwide.espacenet.com.
International Search Report dated Oct. 4, 2010 for Application No. PCT/US2010/043218.
Written Opinion dated Oct. 4, 2010 for Application No. PCT/US2010/043218.

* cited by examiner

*Primary Examiner* — Helen F Heggestad
(74) *Attorney, Agent, or Firm* — Steven J. Goldstein; Frost Brown Todd, LLC

(57) ABSTRACT

The present application discloses microbially-stable solutions of water-solubilized lipophilic vitamins, such as Vitamin E. These solutions contain from about 0.5% to about 30% of a salt selected from potassium chloride, magnesium chloride, calcium chloride, potassium phosphate, calcium phosphate, potassium sulfate, calcium phosphate, magnesium phosphate, magnesium sulfate, potassium iodide, and mixtures of these salts. The method of providing microbially-stable solutions of such water-solubilized lipophilic vitamins, as well as food and beverage products containing those microbially-stabilized water-solubilized lipophilic vitamins, are also disclosed.

10 Claims, No Drawings

MICROBIALLY-STABLE VITAMIN E SOLUTIONS

This application relates to and claims priority from U.S. Provisional Application Ser. No. 61/230,148, filed Jul. 31, 2009, incorporated herein by reference.

TECHNICAL FIELD OF THE INVENTION

The present invention relates to microbially-stable vitamin solutions, particularly Vitamin E solutions that can be used in food and beverage products.

BACKGROUND OF THE INVENTION

When formulating food or beverage compositions, it is frequently useful to add vitamins to round out the nutritional value of the product. Vitamins are either water-soluble (hydrophilic) or fat-soluble (lipophilic). It is a particular challenge to formulate fat-soluble vitamins (such as vitamins A, D, E or K) into aqueous-based products, such as health beverages.

One known approach for formulating lipophilic vitamins into aqueous solutions is to add hydrophilic side chains onto the lipophilic base molecule. By doing that, the hydrophilic-lipophilic balance (HLB) of the entire molecule can be adjusted toward water-solubility, making the molecule water-soluble. An example of such a water-soluble variant of Vitamin E (Tocopherol) is Vitamin E succinate polyethylene glycol (PEG) 1000 (also referred to as Vitamin E TPGS) which has the following formula:

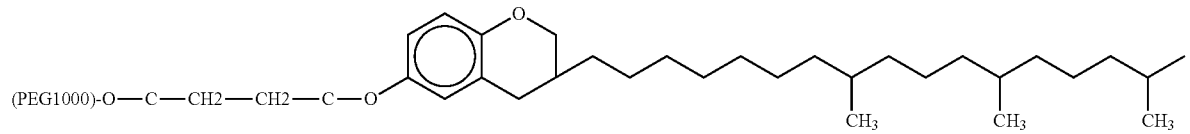

Additional water-soluble variants of Vitamin E can be made by substituting other dicarboxylic acids (such as carbonic acid, oxalic acid, malonic acid, glutaric acid, adipic acid, phthalic acid, glycolic acid, lactic acid, mendelic acid, citric acid and mixtures thereof) for the succinic acid. In addition, the polyethylene glycol component can be adjusted such that it contains from about 200 to about 2000 (preferably about 1000) subunits. Also, polyether materials other than PEG, such as polypropylene glycol containing from about 200 to about 2000 (preferably about 1000) subunits can be used. Further, the PEG and PPG compounds can be provided as monolaurate, monomyristate, monopalmitate or monostearate derivatives. Specific commercially-available water-soluble Vitamin E materials include Vitamin E succinate polyethylene glycol (PEG) 1000.

While these materials can be placed into aqueous solution, they do potentially raise microbial contamination issues. Specifically, upon storage, they can provide an ideal medium for the growth of yeast, bacteria and mold. That contamination issue must be addressed before the materials can be used in food and beverage products. One way to address the issue is to pack the materials aseptically. The additional processing required to do that makes such packaging very expensive. Another way to address the issue is to place broad spectrum preservatives in the solution. While those may be effective, it is preferable not to include preservatives in one component of a finished product, since they might not be optimal for use in the finished product or there might be a desire to formulate the finished product without preservatives. A third way to address this issue is to maintain the pH of the Vitamin E solution very low (i.e., between about 2 and about 4) This, however, causes acid hydrolysis of the Vitamin E, resulting in vitamin loss.

SUMMARY OF THE INVENTION

The present invention provides for aqueous solutions which comprise from about 0.5% to about 30% (by weight) of a water-solubilized derivative of a fat-soluble vitamin selected from Vitamins A, D, E and K (particularly Vitamin E), and from about 0.5% to about 30% (by weight) of a salt selected from KCl, $MgCl_2$, $CaCl_2$, $K_3PO_4$, $Ca_3(PO_4)_2$, $K_2SO_4$, $CaSO_4$, $Mg_3(PO_4)_2$, $MgSO_4$, KI, and mixtures thereof (particularly KCl or KI).

DETAILED DESCRIPTION OF THE INVENTION

The present invention provides a simple, effective and inexpensive way to address this microbial stability issue. This is accomplished by placing an anti-microbially effective amount of potassium chloride (KCl) into the aqueous solution containing the solubilized Vitamin E material. Other salts may be used in place of KCl, as long as they are relatively neutral in pH (pH of from about 6 to about 8, preferably about 7) in solution since, if they are outside this range, they might hydrolyze the ether or ester bonds in the hydrophilic side chain, thereby rendering the vitamin insoluble or ineffective. Examples of such salts that may be used in place of KCl include magnesium chloride ($MgCl_2$), calcium chloride ($CaCl_2$), potassium phosphate ($K_3PO_4$), calcium phosphate ($Ca_3(PO_4)_2$), potassium sulfate ($K_2SO_4$), calcium sulfate ($CaSO_4$), magnesium phosphate ($Mg_3(PO_4)_2$), magnesium sulfate ($MgSO_4$), potassium iodide (KI), or combinations of these materials. In addition to microbially stabilizing the soluble Vitamin E component, the salt can serve as a source of minerals (e.g., potassium, magnesium, calcium) if the material is used in a food or beverage product. While sodium salts can be used herein from an efficacy point of view, such salts are generally avoided because of the health issues (e.g., hypertension) associated with sodium in the diet.

Generally, the aqueous solutions of the present invention will include a concentration of from about 0.5% to about 30% (by weight) of the solubilized Vitamin E component. One embodiment of the solution contains about 20% by weight of the solubilized Vitamin E component. Although inclusion of the solubilized Vitamin E is generally limited by its critical micelle concentration (CMC), the presence of the salt may salt out the micelles formed, even above the CMC, making the solution less viscous and allowing for the use of higher Vitamin E concentrations in the solution. The salt is generally used in the solution at a level of from about 0.5% to about 30% (by weight); in one embodiment, the salt is used at from about 5% to about 20% (by weight), and in another embodiment, the salt is used at from about 10% to about 15% (by weight).

Water-solubilized derivatives of fat-soluble vitamins are known in the art. They can be formulated by adding hydrophilic side chains onto the lipophilic base molecule. By doing that, the hydrophilic-lipophilic balance (HLB) of the entire molecule can be adjusted toward water-solubility, making the molecule water-soluble. An example of such a water-soluble variant of Vitamin E (Tocopherol) is Vitamin E succinate polyethylene glycol (PEG) 1000, which has the following formula:

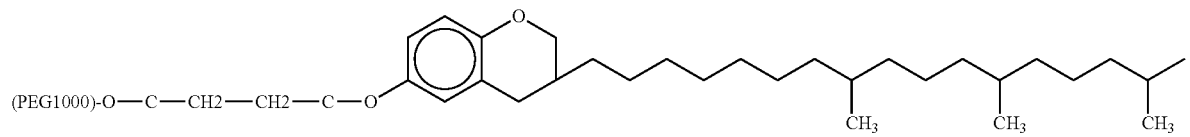

This material is also known as Vitamin E TPGS. Additional water-soluble variants of Vitamin E can be made by substituting other dicarboxylic acids (such as carbonic acid, oxalic acid, malonic acid, glutaric acid, adipic acid, phthalic acid, glycolic acid, lactic acid, mendelic acid, and mixtures thereof) for the succinic acid. In addition, the polyethylene glycol component can be adjusted such that it contains from about 200 to about 2000 (preferably about 1000) subunits. Also, polyether materials other than PEG, such as polypropylene glycol (PPG) containing from about 200 to about 2000 (preferably about 1000) subunits can be used. Further, the PEG and PPG compounds can be provided as monolaurate, monomyristate, monopalmitate or monostearate derivatives. Specific commercially-available water-soluble Vitamin E materials include Vitamin E succinate polyethylene glycol (PEG)1000. A similar approach can be taken to prepare water-soluble versions of other lipophilic vitamins, including Vitamins A, D and K.

Other materials frequently and conventionally found in vitamin and nutritional supplement solutions that can support microbial action can be included, at their art-established levels, in the solutions of the present invention.

Each gram of this solution delivers to the user 2.5-3.0 RDI of d-alpha-tocopherol and 0.022 RDI of potassium.

This technology may be used with fat-soluble vitamins other than Vitamin E, specifically with Vitamins A, D and K.

The vitamin solutions defined herein may be added, in nutritionally effective levels, to food and beverage products to provide supplementation of those products. Conventionally known food and beverage products may be used.

The following non-limiting examples are illustrative of the present invention.

Example 1

Control

A solution is prepared by utilizing 800 grams of de-ionized water to which 200 grams of chipped Vitamin E TPGS is added. The mixture is warmed to a temperature of 37° C. and mixed until all of the Vitamin E has dissolved and a uniform solution is produced. Samples of this mixture are then assessed for microbial susceptibility by subjecting the solution to a 3 week micro challenge utilizing *Candida albicans, Aspergillus brasiliensis, Escherichia coli* and *Staphylococcus aureus*. Results show that organisms can proliferate in the unpreserved Vitamin E solution.

| | | CHALLENGE STUDY RESULTS TEMPERATURE = AMBIENT (20-25° C.) | | | | | | |
|---|---|---|---|---|---|---|---|---|
| | | INITIAL COUNT CFU/gm (prior to inoculation) | | | TIME INTERVAL | | | |
| INOCULATING ORGANISM(S) | INOCULUM LEVEL (CFU/gm of sample) | APC | Yeast | Mold | Week 0 | Week 1 | Week 2 | Week 3 |
| *Candida albicans* ATCC 10231 | $3.4 \times 10^5$ | 660 | 30 | 60 | $8.2 \times 10^5$ | $8.6 \times 10^5$ | $1.2 \times 10^6$ | $9.6 \times 10^5$ |
| *Aspergillus brasiliensis* ATCC 16404 | $1.0 \times 10^5$ | | | | $2.8 \times 10^5$ | $3.4 \times 10^5$ | $2.6 \times 10^5$ | $2.3 \times 10^5$ |
| *Escherichia coli* ATCC 9896 | $4.3 \times 10^6$ | | | | $3.1 \times 10^6$ | $1.6 \times 10^7$ | $8.0 \times 10^6$ | $5.9 \times 10^6$ |
| *Staphylococcus aureus* ATCC 6538 | $6.5 \times 10^6$ | | | | $1.3 \times 10^7$ | $1.2 \times 10^6$ | $2.7 \times 10^5$ | $1.7 \times 10^6$ |
| APPEARANCE | | | | | Normal | *Aspergillus brasiliensis* visible mold growth | *Aspergillus brasiliensis* visible mold growth | *Aspergillus brasiliensis* visible mold growth *S. aureus*: turbid |

One embodiment of the present invention is an aqueous solution which contains about 20% (by weight) Vitamin E succinate-PEG1000, and about 15% (by weight) potassium chloride. The product is clear, has good viscosity and inhibits the growth of mold, yeast and bacteria for at least 24 months.

Example 2

In a second test, a solution is prepared by utilizing 700 grams of de-ionized water to which 100 grams of potassium chloride is added and solubilized. The mixture is warmed to a temperature of 37° C. To this, 200 grams of chipped Vitamin E TPGS is added. The mixture is mixed until all of the Vitamin E has dissolved and a uniform solution is produced. Samples of this mixture are then assessed for microbial susceptibility by subjecting the solution to a 12 week micro challenge utilizing *Candida albicans, Aspergillus brasiliensis, Escherichia coli* and *Staphylococcus aureus*. Results show control of the tested organisms, thereby demonstrating hostility.

| | | INITIAL COUNT CFU/gm | | | | | | | | | |
|---|---|---|---|---|---|---|---|---|---|---|---|
| | INOCULUM | | | | | | | | | | |
| INOCULATING | LEVEL (CFU/gm | (prior to inoculation) | | | | | TIME INTERVAL | | | | |
| ORGANISM(S) | of sample) | APC | Yeast | Mold | Week 0 | Week 1 | Week 2 | Week 3 | Week 4 | Week 8 | Week 12 |
| *Candida albicans* ATCC 10231 | $2.2 \times 10^5$ | <10 | <10 | <10 | $2.7 \times 10^5$ | $7.0 \times 10^4$ | $1.2 \times 10^5$ | $9.4 \times 10^4$ | $5.8 \times 10^4$ | $6.0 \times 10^5$ | $5.1 \times 10^4$ |
| *Aspergillus brasiliensis* ATCC 16404 | $3.0 \times 10^5$ | | | | $4.4 \times 10^5$ | $4.0 \times 10^5$ | $8.6 \times 10^5$ | $7.4 \times 10^5$ | $6.8 \times 10^5$ | $4.6 \times 10^4$ | $7.4 \times 10^4$ |
| *Escherichia coli* ATCC 8739 | $1.1 \times 10^7$ | | | | $1.0 \times 10^7$ | $2.2 \times 10^4$ | $2.8 \times 10^3$ | <10 | <10 | <10 | <10 |
| *Staphylococcus aureus* ATCC 6538 | $2.0 \times 10^7$ | | | | $1.3 \times 10^7$ | $1.7 \times 10^6$ | $4.9 \times 10^3$ | 20 | <10 | <10 | <10 |
| APPEARANCE | | | | | Normal | Normal | Normal | Normal | Normal | Normal | *A. brasiliensis* growth settled to bottom of tube. All others normal. |

CHALLENGE STUDY RESULTS
TEMPERATURE = AMBIENT (20-25° C.)

Example 3

In a third test, a solution is prepared by utilizing 650 grams of de-ionized water to which 150 grams of potassium chloride is added and solubilized. The mixture is warmed to a temperature of 40° C. To this, 200 grams of chipped Vitamin E TPGS is added. The mixture is mixed until all of the Vitamin E has dissolved and a uniform solution is produced. Samples of this mixture are then assessed for microbial susceptibility by subjecting the solution to a 12 week micro challenge utilizing *Candida albicans, Aspergillus brasiliensis, Escherichia coli* and *Staphylococcus aureus*. Results show good control of the tested organisms, thereby demonstrating hostility.

Example 4

A solution of vitamin E TPGS is prepared in advance and stored by combining 650.0 grams of deionized water, 150.0 grams of potassium chloride and 200.0 grams of vitamin E TPGS. The mixture is heated to 35° C., mixed until uniform, cooled to ambient and stored for several weeks before use.

A beverage product is prepared by combining and mixing the following ingredients:

| Ingredients | Wt % |
|---|---|
| Citric acid | 0.130 |
| Preservative | 0.096 |
| Sucralose | 0.036 |
| Fiber | 0.0570 |
| Potassium citrate | 0.024 |
| Potassium chloride | 0.104 |
| Flavor | 0.080 |

CHALLENGE STUDY RESULTS
TEMPERATURE = AMBIENT (20-25° C.)

| | | INITIAL COUNT CFU/gm | | | | | | | | | |
|---|---|---|---|---|---|---|---|---|---|---|---|
| | INOCULUM | | | | | | | | | | |
| INOCULATING | LEVEL (CFU/gm | (prior to inoculation) | | | | | TIME INTERVAL | | | | |
| ORGANISM(S) | of sample) | APC | Yeast | Mold | Week 0 | Week 1 | Week 2 | Week 3 | Week 4 | Week 8 | Week 12 |
| *Candida albicans* ATCC 10231 | $1.0 \times 10^6$ | 20 | <10 | <10 | $6.0 \times 10^5$ | $8.6 \times 10^4$ | $1.6 \times 10^3$ | $1.0 \times 10^2$ | $1.0 \times 10^2$ | <10 | <10 |
| *Aspergillus brasiliensis* ATCC 16404 | $6.6 \times 10^4$ | | | | $1.9 \times 10^5$ | $1.8 \times 10^5$ | $2.5 \times 10^5$ | $3.1 \times 10^5$ | $3.0 \times 10^5$ | $2.6 \times 10^5$ | $5.0 \times 10^4$ |
| *Escherichia coli* ATCC 8739 | $8.0 \times 10^6$ | | | | $8.0 \times 10^6$ | $2.0 \times 10^1$ | <10 | <10 | <10 | <10 | <10 |
| *Staphylococcus aureus* ATCC 6538 | $3.2 \times 10^6$ | | | | $4.2 \times 10^6$ | $1.2 \times 10^5$ | 20 | <10 | <10 | <10 | <10 |
| APPEARANCE | | | | | Normal | Normal | Normal | Normal | Normal | Normal | Normal |

| Ingredients | Wt % |
| --- | --- |
| Potassium ascorbate | 0.020 |
| Calcium D-pantothenate | 0.002 |
| Vitamin E solution (stabilized) - defined above | 0.100 |
| Deionized water | QS |

Example 5

A solution of vitamin E TPGS is prepared and stored by combining 650.0 grams of deionized water, 149.5 grams of potassium chloride, 0.5 grams of potassium iodine and 200.0 grams of vitamin E TPGS. The mixture is heated to 30° C., mixed until uniform, cooled to ambient and stored for use.

A beverage product is prepared by combining and mixing the following ingredients:

| Ingredients | Wt % |
| --- | --- |
| Citric acid | 0.120 |
| Preservative | 0.080 |
| High Fructose Corn Syrup | 0.110 |
| Natural Color | 0.008 |
| Potassium citrate | 0.024 |
| Potassium chloride | 0.104 |
| Flavor | 0.080 |
| Potassium ascorbate | 0.020 |
| Calcium D-pantothenate | 0.002 |
| Vitamin E solution (stabilized) - defined above | 0.110 |
| Deionized water | QS |

What is claimed is:

1. An aqueous solution which comprises from about 0.5% to about 30% (by weight) of a water-solubilized Vitamin E material, and from about 0.5% to about 30% (by weight) of a salt selected from KCl, $MgCl_2$, $CaCl_2$, $K_3PO_4$, $CaSO_4$, $Ca_3(PO_4)_2$, $K_2SO_4$, $CaSO_4$, $Mg_3(PO_4)_2$, $MgSO_4$, KI, and mixtures thereof; wherein the water-solubilized Vitamin E material is Vitamin E succinate PEG1000.

2. The aqueous solution according to claim 1 wherein the salt is selected from KCl, KI and mixtures thereof.

3. The aqueous solution according to claim 2 wherein the salt is KCl.

4. The aqueous solution according to claim 3 which includes about 20% Vitamin E succinate-PEG1000, and about 15% KCl.

5. A food composition comprising a nutritionally effective level of the solution of claim 4.

6. A food product comprising a nutritionally effective level of the solution of claim 1.

7. A method of providing a microbially-stable aqueous solution of a water-soluble Vitamin E material, comprising adding from about 0.5% to about 30% (by weight) of a salt selected from KCl, $MgCl_2$, $CaCl_2$, $K_3PO_4$, $Ca_3(PO_4)_2$, $K_2SO_4$, $CaSO_4$, $Mg_3(PO_4)_2$, $MgSO_4$, KI, and mixtures thereof, to said solution; wherein the water-solubilized Vitamin E material is Vitamin E succinate PEG 1000.

8. A method according to claim 7 wherein the salt is selected from KCl, KI and mixtures thereof.

9. A method of providing Vitamin E supplementation of a food or beverage product by adding a nutritionally effective amount of the solution of claim 1 to said food or beverage product.

10. An aqueous-based beverage product comprising a nutritionally effective level of an aqueous solution which comprises from about 0.5% to about 30% (by weight) of a water-solubilized Vitamin E material, and from about 0.5% to about 30% (by weight) of a salt selected from KCl, $MgCl_2$, $CaCl_2$, $K_3PO_4$, $CaSO_4$, $Ca_3(PO_4)_2$, $K_2SO_4$, $CaSO_4$, $Mg_3(PO_4)_2$, $MgSO_4$, KI, and mixtures thereof, wherein the water-solubilized Vitamin E material is Vitamin E succinate PEG 1000.

* * * * *